United States Patent [19]

Ross

[11] Patent Number: 4,787,848
[45] Date of Patent: Nov. 29, 1988

[54] METHOD AND APPARATUS FOR DRILLING BORES IN JAW BONE TISSUE FOR THE RECEPTION OF DENTAL ANCHORS

[75] Inventor: Stanley E. Ross, Boca Raton, Fla.

[73] Assignee: Ross Systems Corporation, Palm Beach, Fla.

[21] Appl. No.: 934,638

[22] Filed: Nov. 25, 1986

[51] Int. Cl.⁴ .............................................. A61C 3/02
[52] U.S. Cl. .................................. 433/165; 433/174; 433/215
[58] Field of Search ............... 433/165, 166, 215, 174; 408/703, 219, 220, 202

[56] References Cited

U.S. PATENT DOCUMENTS

| | | | |
|---|---|---|---|
| 716,441 | 12/1902 | Latham | 408/223 |
| 1,216,683 | 2/1917 | Greenfield | 433/165 |
| 2,280,927 | 4/1942 | Phillips | 433/165 |
| 3,320,832 | 5/1967 | Jensen | 408/202 |
| 3,534,476 | 10/1970 | Winters | 433/165 |
| 3,645,642 | 2/1972 | Koslow | 408/202 |
| 4,431,416 | 2/1984 | Niznick | 433/174 |
| 4,526,542 | 7/1985 | Kochis | 433/165 |

FOREIGN PATENT DOCUMENTS 302233 10/1954 Switzerland .

Primary Examiner—John J. Wilson
Attorney, Agent, or Firm—Burns, Doane, Swecker & Mathis

[57] ABSTRACT

A bore is formed in the jaw bone of a patient by means of a trephine drill having a hollow head. A pilot hole is initially drilled in the jaw bone and a guide bushing is installed in the pilot hole. The drill head is inserted telescopingly over a guide portion of the bushing and is advanced into the bone until the drill head abuts an end of the guide portion to terminate drill advancement. The length of the bore is extended by advancing the drill further into the bone relative to a stop member which is freely longitudinally slidably situated on the drill. When the stop member becomes sandwiched between the jaw bone and a surface movable with a motor housing carrying the drill, it is assured that the desired bore depth has been obtained.

5 Claims, 2 Drawing Sheets

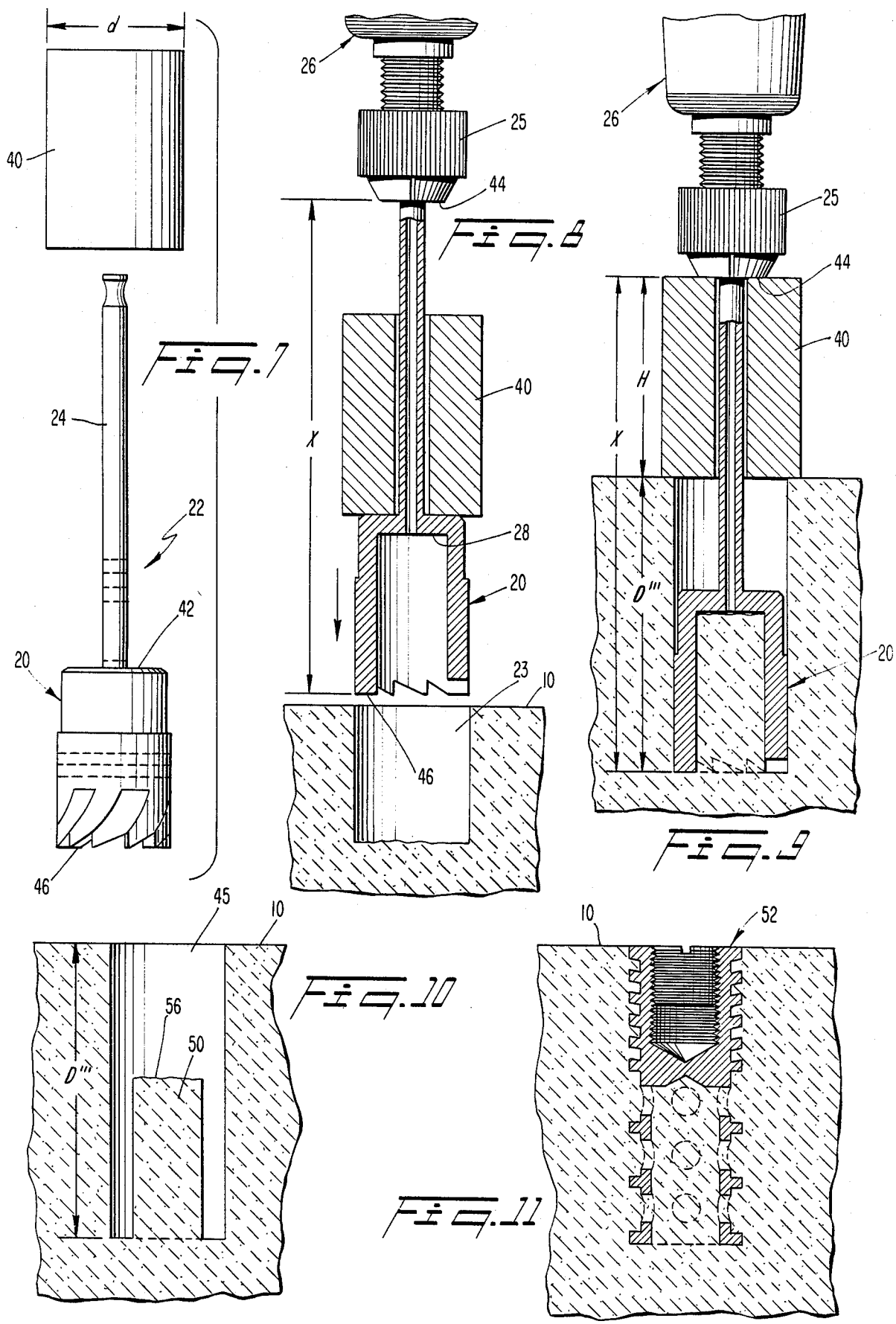

METHOD AND APPARATUS FOR DRILLING BORES IN JAW BONE TISSUE FOR THE RECEPTION OF DENTAL ANCHORS

BACKGROUND AND OBJECTS OF THE INVENTION

The present invention relates to the drilling of bores in jaw bone tissue in preparation for the insertion of dental anchors.

One technique for the installation of dental prostheses involves drilling a bore into a patient's jaw bone and the insertion of a dental anchor into the bore. The bore is formed with a core of bone on the floor of the bore which fits into a recess in the front end of the anchor. Eventually, bone tissue grows against the anchor to fixedly secure the anchor in place. Techniques of this type are disclosed in U.S. Pat. No. 4,431,416 and copending U.S. application Serial Nos. 06/896,101 and 06/896,524 filed Aug. 13, 1986.

The bore, which is drilled in such fashion as to leave a center core therein, is drilled in three stages. In the first stage, a pilot hole is made by a drill bit. Then, within the pilot hole is installed a guide bushing which comprises two cylinders attached end-to-end. One of the cylinders is of small diameter and is inserted into the pilot hole. The drill head of a trephine drill is inserted over the large diameter cylinder in telescoping fashion and is advanced into the bone tissue during a second stage of the operation. The large diameter cylinder acts as a guide for the trephine drill to prevent the latter from moving sideways. The drill is advanced to a depth short of the final depth and, when removed, leaves a center core of bone. A hand tool is then inserted into the bore in order to break-off the core. Then, during the final step, the drill is reinserted into the bore and advanced to a final depth.

It is necessary that the bore be made sufficiently deep to receive the anchor, but not so deep that a nerve may be cut and damaged. This requires a certain drilling precision which, to date, has been difficult to achieve.

At present, it is conventional to employ a trephine drill which has markings on its side to indicate the depth attained by the drill. However, it is difficult for an operator to accurately see the markings during a drilling procedure, requiring the operator to repeatedly interrupt the drilling procedure to check the marks. Such a practice is time-consuming and does not guarantee that the required depth will not be exceeded.

It has been proposed in Swiss Pat. No. 302,233 to terminate the advancement of a drill by means of a stop adjustably fixed on the drill. However, i is difficult and time-consuming to adjust the stop to a precise position on the drill. Also, since the stop is fixed by a set screw, it is possible that if the set screw becomes inadvertently loosened, allowing the stop to move, severe damage can result from excessive advancement into the jaw bone.

It would be desirable to provide drilling apparatus and methods which enable a bore to be drilled quickly to the desired depth, with absolutely no chance whatsoever that the desired depth could be exceeded to any appreciable extent.

SUMMARY OF THE INVENTION

The present invention relates to methods and apparatus for drilling a bore of predetermined depth in a jaw bone of a patient so that a dental anchor can be installed therein. The method comprises the steps of drilling a longitudinally extending pilot hole in the bone. A bushing is installed in the pilot hole. The bushing comprises first and second cylindrical portions arranged end-to-end. The first cylindrical portion is inserted into the pilot hole such that the second cylindrical portion bears against the bone. A hollow head of a trephine drill is inserted in telescoping fashion over the second cylindrical portion such that the second cylindrical portion restrains the drill against sideways motion. The drill head is advanced longitudinally into the jaw bone until an abutment shoulder of the drill abuts an end of the second cylindrical portion to form a bore of a desired first depth, which is less than the predetermined depth. The bore contains a first core portion. The drill is removed from the bore, and the first core portion is broken and removed from the bore. The drill head is reinserted into the bore and advanced longitudinally to extend the depth of the bore while forming a second core portion therein.

In another aspect of the present invention, the step of extending the depth of the bore is achieved by advancing the drill head longitudinally relative to a stop member which is freely longitudinally slidably situated on the drill, until the stop member becomes sandwiched between the jaw bone and a surface movable with a motor housing carrying the drill. The stop member has an outer diameter greater than an outer diameter of the drill head, and has a longitudinal length of such dimension that when that length is subtracted from a longitudinal distance between a front end of the drill head and the surface movable with the motor housing, the remainder equals the predetermined depth of the bore.

The present invention also involves a dental drilling assembly for drilling a bore of predetermined depth into a jaw bone of a patient so that a dental anchor can be installed therein. The assembly comprises a drill motor housing, a trephine drill, and a stop member. The trephine drill is mounted in the housing for rotation about a longitudinal axis and includes a hollow drill head for drilling a bore having a central core. The stop member is situated for free longitudinal sliding movement on the drill and is arranged to terminate longitudinal advancement of the drill into the jaw bone upon becoming sandwiched between the jaw bone and a surface movable with the motor housing. The stop member has an outer diameter greater than an outer diameter of the drill head, and has a longitudinal length of such dimension that when the height is subtracted from a longitudinal distance between a front end of the drill head and the surface movable with the motor housing, the remainder equals the predetermined depth of the bore.

BRIEF DESCRIPTION OF THE DRAWINGS

The objects and advantages of the invention will become apparent from the following detailed description of a preferred embodiment thereof, in connection with the accompanying drawings, in which like numerals designate like elements, and in which:

FIG. 7 is an exploded side elevational view of a trephine drill and a stop which is to be installed thereon;

FIG. 8 is a view of the trephine drill, with the stop mounted thereon, the drill being mounted in the chuck of a drill motor and is being advanced into the initial bore;

FIG. 9 is a view similar to FIG. 8 after the drill head has been advanced sufficiently far to form a final bore;

FIG. 10 is a cross-sectional view through the jaw bone depicting the final bore; and FIG. 11 is a sectional view through the jaw bone after a dental anchor has been installed in the final bore, and the bone tissue has grown against the dental anchor.

DETAILED DESCRIPTION OF A PREFERRED EMBODIMENT OF THE INVENTION

Figure 1:
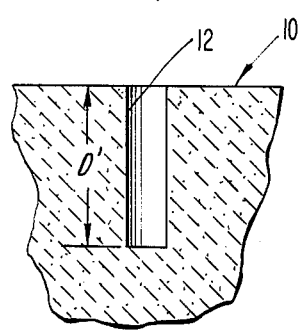
FIG. 1 is a cross-sectional view taken through the jaw bone of a patient after a pilot hole has been drilled therein.
Figure 2:
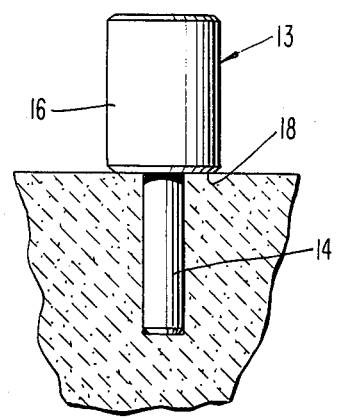
FIG. 2 is a view similar to FIG. 1 after a guide bushing has been inserted into the pilot hole.

Depicted in FIG. 1 is a jaw bone of a patient in which a dental anchor is to be installed. In a first stage of the operation, a pilot hole 12 drilled to a predetermined depth D' to enable a guide bushing 13 to be installed. The bushing, depicted in FIG. 2, includes first and second cylindrical sections 14, 16, one section 14 being of smaller diameter than the other 16. The diameter of the pilot hole 12 is sufficiently large to receive the small section 14 of the bushing and sufficiently deep to enable an end 18 of the large section 16 to abut the bone tissue 10.

Figure 3:
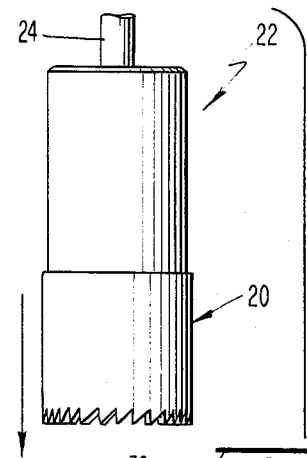
FIG. 3 is a view similar to FIG. 2 as the head of a trephine drill is being installed onto a large cylindrical portion of the bushing.

The diameter of the large section 16 corresponds to the inner diameter of a hollow drill head 20 of a trephine drill 22 to enable that hollow head of the drill to be inserted telescopingly over the large section 16 of the bushing (FIG. 3). Thus, the drill is constrained against sideways (radial) movement. The trephine drill 22 includes a shank 24 mounted in a chuck 25 of a hand-held motor housing 26 and is advanced into the jaw bone while the large section 16 of the bushing prevents sideways movement of the drill.

As noted earlier, the operation described thus far is conventional. That is, in conventional practice, the drill is advanced longitudinally to a desired depth D'', which depth D'' is monitored by the operator who must view markings provided along the side of the drill 22. That practice is time-consuming and can be imprecise since the possibility exists for the operator to exceed the desired depth. The depth reached during this stage of drilling determines the depth of the top face of the bone core to be formed in the final bore.

Figure 4:
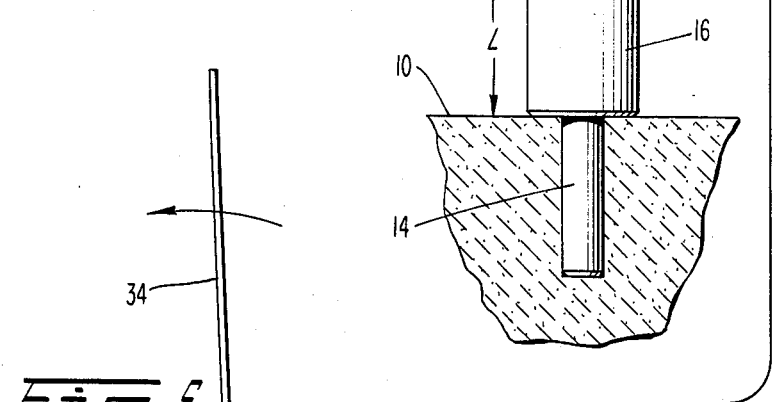
FIG. 4 is a view similar to FIG. 3 after the trephine drill has advanced into the bone tissue to form an initial bore therein and has contacted an end of the large diameter portion of the bushing.
Figure 4:
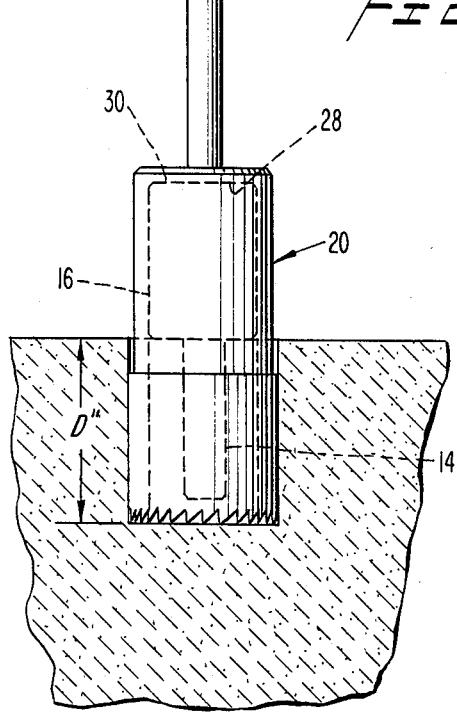

In accordance with the present invention, however, the longitudinal length L of the guide section 16 corresponds to the desired depth D'' to be attained during this drilling stage. Thus, when an inner shoulder 28 within the drill head 20 abuts against a stop surface 30 of the guide section 16, the drilling advancement ceases at the current drilling depth D'' (FIG. 4).

Figure 5:
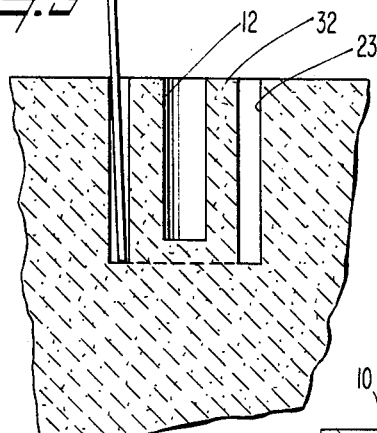
FIG. 5 is a sectional view taken through the jaw bone depicting the initial bore which has been formed, as a tool is in the process of breaking off a core portion of the initial portion.
Figure 6:
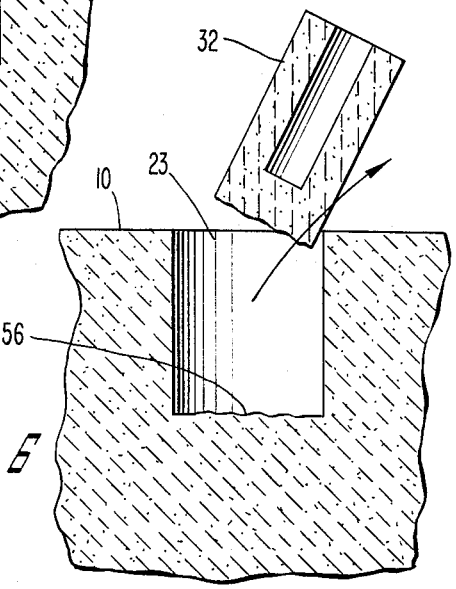
FIG. 6 is a view similar to FIG. 5 as the broken core portion is being removed from the initial bore.

At this point, the drill 22 and bushing 13 are removed from the initial bore 23 which bore contains an unwanted center core 32 of bone tissue. Accordingly, a hand-held tool 34 is inserted into the bore (FIG. 5) to apply sideways pressure to the core 32 which breaks off and is removed (FIG. 6).

In the next drilling stage, the depth of the initial bore 23 is extended. Importantly, the final depth of the bore must not exceed a predetermined depth D''' in order to absolutely prevent any chance that a nerve will be contacted and damaged.

In accordance with the present invention, a stop member 40 is loosely situated on the drill shank 24 atop the drill head 20 for free longitudinal sliding movement between a top surface 42 of the drill head and an end face 44 of the motor housing. The stop member can be installed before or after the drilling of the initial bore 23. The stop has an outer diameter d larger than that of the drill head 20. The length H of the stop 40 is chosen to assure that the longitudinal advancement of the drill terminates when the desired bore depth D''' has been reached. This is achieved by matching the stop to the drill itself. Since the distance X from the front end 46 of the drill to the end face 44 of the chuck is constant and known, the presence of the stop 40 will reduce the extent of travel of the drill by an amount equal to the length H of the stop. In other words, X minus H equals the desired predetermined depth D''' of the bore 23. Hence, a set of stops of different lengths can be prepared to create a variety of drilling depths D'''. As the drilling progresses, the stop 40 will eventually become sandwiched between the end face 44 of the drill chuck and the jaw bone 10 (FIG. 9) to prevent further advancement of the drill 22, whereupon the drill is removed (FIG. 10). A core 50 of bone tissue remains in the final bore 45.

The dental anchor 52 is then be inserted into the final bore as depicted in FIG. 11 wherein the core 50 enters a hollow front end 54 thereof. Eventually, the bone tissue grows against the anchor 52 to permanently retain the anchor 52 in the jaw bone 10.

It will be appreciated that the stop member 40 of the present invention absolutely assures that the predetermined drilling depth D''' will not be exceeded. This is achieved without the need for an operator to monitor any difficult-to-see markings on the drill. Nor is there any need for a set screw to secure the stop member nor the concern that such a set screw could become inadvertently loosened.

The guide bushing 13 assures that the end surface 56 of the core 50 in the final bore 45 will be at the proper depth. Again, this is achieved without any need for the operator to monitor depth markings on the side of the drill.

Although the present invention has been described in connection with a preferred embodiment thereof, it will be appreciated by those skilled in the art that additions, modifications, substitutions and deletions not specifically described, may be made without departing from the spirit and scope of the invention as defined in the appended claims.

What is claimed is:

1. A method of drilling a bore of predetermined depth in a jaw bone of patient so that a dental anchor can be installed therein, said method comprising the steps of advancing a hollow head of a trephine drill longitudinally into the jaw bone to form a bore having a center core, said advancing step being continued relative to a stop member which is loosely mounted on a shank portion of said drill so as to be freely longitudinally slidable thereon until said stop member becomes sandwiched between the jaw bone and a surface movable with a motor housing carrying said drill, said shank portion being of smaller diameter than said drill head and extending from said drill head to a chuck portion of said motor housing, said stop member having an outer diameter greater than an outer diameter of said drill head and having a longitudinal length of such dimension that when said length is subtracted from a longitudinal distance between a front end of said drill head and said surface movable with said motor housing, the remainder equals said predetermined depth.

2. A method of drilling a bore of a predetermined depth in a jaw bone of a patient so that a dental anchor can be installed therein, said method comprising the steps of:

drilling a longitudinally extending pilot hole in the bone, installing in said pilot hole a bushing comprising first and second cylindrical portions arranged end-to-end, said first cylindrical portion being inserted into said pilot hole such that said second cylindrical portion bears against the bone, inserting a hollow head of a trephine drill in telescoping fashion over said second cylindrical portion such that said second cylindrical portion restrains said drill against sideways motion, advancing said drill head longitudinally into the jaw bone until an abutment shoulder of said drill abuts an end of said second cylindrical portion to form a bore of a desired first depth, which is less than said predetermined depth, said bore containing a first core portion, removing said drill from said bore, breaking off and removing said first core portion, and reinserting said drill head into said bore and advancing said drill head longitudinally to extend the depth of said bore while forming a second core portion therein, said advancing step being continued relative to a stop member which is freely longitudinally slidably situated on said drill until said stop member becomes sandwiched between the jaw bone and a surface movable with a motor housing carrying said drill, said stop member having an outer diameter greater than an outer diameter of said drill head, and having a longitudinal length of such dimension that when said length is subtracted from a longitudinal distance between a front end of said drill head and said surface movable with said motor housing, the remainder equals said predetermined depth.

3. A method according to claim 2, wherein said stop member sides freely on a shank portion of said drill, said shank portion being of smaller diameter than said drill head and extending from said drill head to a chuck portion of said motor housing.

4. A method of drilling a bore of predetermined depth in a jaw bone of a patient so that a dental anchor can be installed therein, said method comprising the steps of:

drilling a longitudinally extending pilot hole in the bone, installing in said pilot hole a bushing comprising first and second cylindrical portions arranged end-to-end, said first cylindrical portion being inserted into said pilot hole such that said second cylindrical portion bears against the bone, inserting a hollow head of a trephine drill in telescoping fashion over said second cylindrical portion such that said second cylindrical portion restrains said drill against sideways motion, advancing said drill head longitudinally into the jaw bone until an abutment shoulder of said drill abuts an end of said second cylindrical portion to form a bore of a desired first depth, which is less than said predetermined depth, said bore containing a first core portion, removing said drill from said bore, breaking off and removing said first core position, and reinserting said drill head into said bore and' advancing said drill head longitudinally to extend the depth of said bore while forming a second core portion therein.

5. A dental drilling assembly for drilling a bore of predetermined depth into a jaw bone of a patient so that a dental anchor can be installed therein, said assembly comprising:

a drill motor housing, a trephine drill mounted in said housing for rotation about a longitudinal axis and including a shank portion and a hollow drill head disposed at an end of said shank portion for drilling a bore having a central core, and a stop member loosely mounted on said drill shank so as to be freely longitudinally slidable thereon and arranged to terminate longitudinal advancement of said drill into the jaw bone upon becoming sandwiched between the jaw bone and a surface movable with said motor housing, said shank portion being of smaller diameter than said drill head and extending from said drill head to a chuck portion of said motor housing, said stop member having an outer diameter greater than an outer diameter of said drill head, and having a longitudinal length of such dimension that when said height is subtracted from a longitudinal distance between a front end of said drill head and said surface movable with said motor housing, the remainder equals said predetermined depth.

* * * * *